(12) United States Patent
Brosnan et al.

(10) Patent No.: US 10,741,284 B2
(45) Date of Patent: Aug. 11, 2020

(54) UNIVERSAL CALIBRATION SYSTEM

(71) Applicant: Stryker Corporation, Kalamazoo, MI (US)

(72) Inventors: Daniel Vincent Brosnan, Kalamazoo, MI (US); Aaron Douglas Furman, Kalamazoo, MI (US); Janani Gopalkrishnan, Portage, MI (US); Mark Richard Bryant, LaOtto, IN (US)

(73) Assignee: Stryker Corporation, Kalamazoo, MI (US)

( * ) Notice: Subject to any disclaimer, the term of this patent is extended or adjusted under 35 U.S.C. 154(b) by 211 days.

(21) Appl. No.: 15/272,590

(22) Filed: Sep. 22, 2016

(65) Prior Publication Data
US 2017/0098048 A1 Apr. 6, 2017

Related U.S. Application Data

(60) Provisional application No. 62/236,424, filed on Oct. 2, 2015.

(51) Int. Cl.
*G16H 40/63* (2018.01)
*G05B 15/02* (2006.01)

(52) U.S. Cl.
CPC ............. *G16H 40/63* (2018.01); *G05B 15/02* (2013.01)

(58) Field of Classification Search
None
See application file for complete search history.

(56) References Cited

U.S. PATENT DOCUMENTS

| | | | |
|---|---|---|---|
| 4,665,573 A | 5/1987 | Fiore | |
| 4,876,490 A | 10/1989 | Kolb | |
| 5,095,562 A | 3/1992 | Alexander | |
| 5,579,547 A | 12/1996 | Hunt | |
| 5,624,000 A | 4/1997 | Miller | |
| 5,898,288 A * | 4/1999 | Rice ..................... | G05B 19/21 318/400.12 |
| 6,334,442 B1 | 1/2002 | Altamura | |
| 7,065,816 B2 | 6/2006 | McGettigan | |
| 7,570,152 B2 | 8/2009 | Smith et al. | |
| 7,690,056 B2 | 4/2010 | Moffa et al. | |

(Continued)

FOREIGN PATENT DOCUMENTS

| | | |
|---|---|---|
| CA | 2393880 A1 | 1/2004 |
| CA | 2529091 A1 | 12/2004 |

(Continued)

OTHER PUBLICATIONS

Troy-Bilt LLC, "Troy-Bilt Flex, a Whole New Approach to Yard Care", URL: http://www.troybilt.com/equipment/troybilt/flex.

(Continued)

*Primary Examiner* — Isaac T Tecklu
(74) *Attorney, Agent, or Firm* — Warner Norcross + Judd LLP

(57) ABSTRACT

A medical support control system comprises a medical support having memory and a control system in connection with the memory and for connection with a component for use at the medical support. The medical support control system further includes a detection system configured to detect when the component is connected to the control system, such as the control system microprocessor.

21 Claims, 11 Drawing Sheets

(56) References Cited

U.S. PATENT DOCUMENTS

| | | | |
|---|---|---|---|
| 7,690,059 B2* | 4/2010 | Lemire | A61G 7/005 5/600 |
| 7,702,481 B2* | 4/2010 | Dionne | A61G 7/015 702/150 |
| 7,774,215 B2 | 8/2010 | Rosow et al. | |
| 7,856,758 B2 | 12/2010 | Ressel et al. | |
| 8,011,039 B2 | 9/2011 | Stryker et al. | |
| 8,060,274 B2 | 11/2011 | Boss et al. | |
| 8,121,856 B2* | 2/2012 | Huster | G06F 19/3418 705/2 |
| 8,334,779 B2 | 12/2012 | Zerhusen et al. | |
| 8,756,078 B2 | 6/2014 | Collins, Jr. et al. | |
| 8,757,308 B2 | 6/2014 | Bhai et al. | |
| 8,914,924 B2 | 12/2014 | Stryker et al. | |
| 9,079,505 B1 | 7/2015 | Hyde et al. | |
| 9,123,229 B2 | 9/2015 | Slavin et al. | |
| 9,230,421 B2 | 1/2016 | Reeder | |
| 9,539,156 B2 | 1/2017 | Lemire et al. | |
| 9,569,591 B2 | 2/2017 | Vanderpohl, III | |
| 9,642,759 B2 | 5/2017 | Stryker et al. | |
| 9,713,728 B2 | 7/2017 | Smith | |
| 2002/0151990 A1* | 10/2002 | Ulrich | G06F 19/3418 700/65 |
| 2004/0172182 A1 | 9/2004 | Pathare | |
| 2005/0113996 A1 | 5/2005 | Pillar et al. | |
| 2006/0049936 A1* | 3/2006 | Collins, Jr. | A61B 5/1115 340/539.11 |
| 2006/0136105 A1 | 6/2006 | Larson | |
| 2007/0010719 A1* | 1/2007 | Huster | G06F 19/3418 600/300 |
| 2007/0174964 A1 | 8/2007 | Lemire et al. | |
| 2007/0210917 A1* | 9/2007 | Collins, Jr. | A61B 5/1117 340/539.1 |
| 2008/0312971 A2 | 12/2008 | Rosow et al. | |
| 2009/0063183 A1* | 3/2009 | McNeely | A61G 12/00 705/2 |
| 2009/0064417 A1 | 3/2009 | Garman | |
| 2009/0088924 A1 | 4/2009 | Coffee et al. | |
| 2010/0117039 A1 | 5/2010 | Perrett et al. | |
| 2001/0208541 | 8/2011 | Wilson et al. | |
| 2011/0208541 A1 | 8/2011 | Wilson et al. | |
| 2011/0301807 A1 | 12/2011 | Staaf | |
| 2012/0123951 A1 | 5/2012 | Hyatt et al. | |
| 2012/0137436 A1 | 6/2012 | Andrienko | |
| 2013/0142367 A1 | 6/2013 | Berry et al. | |
| 2013/0191032 A1* | 7/2013 | Marquardt | G06F 11/0796 702/19 |
| 2013/0249458 A1 | 9/2013 | Abou-Kasm et al. | |
| 2014/0080413 A1 | 3/2014 | Hayes et al. | |
| 2014/0259414 A1 | 9/2014 | Hayes et al. | |
| 2014/0297327 A1 | 10/2014 | Heil et al. | |
| 2014/0320290 A1 | 10/2014 | Reeder et al. | |
| 2015/0115638 A1 | 4/2015 | Lambarth et al. | |
| 2015/0135436 A1* | 5/2015 | Stryker | A61G 7/05 5/600 |
| 2015/0239365 A1 | 8/2015 | Hyde et al. | |
| 2015/0281659 A1 | 10/2015 | Hood et al. | |
| 2016/0013837 A1 | 1/2016 | Howell et al. | |
| 2016/0259906 A1 | 9/2016 | Iucha et al. | |
| 2016/0283681 A1 | 9/2016 | Falck et al. | |
| 2016/0331614 A1 | 11/2016 | Furman et al. | |
| 2017/0027797 A1* | 2/2017 | Dolliver | A61G 13/04 |
| 2017/0098048 A1 | 4/2017 | Brosnan et al. | |
| 2018/0161225 A1 | 6/2018 | Zerhusen et al. | |

FOREIGN PATENT DOCUMENTS

| | | |
|---|---|---|
| EP | 553372 A1 | 1/1992 |
| EP | 553372 A1 | 8/1993 |
| KR | 20130076922 A | 7/2013 |
| WO | 9834577 | 8/1998 |
| WO | 2004/021952 A2 | 3/2004 |
| WO | 2004021952 A2 | 3/2004 |

OTHER PUBLICATIONS

Hovertech International, "Safe Bariatric Patient Handling", Jul. 2013; 2 pages.

Stryker Corporation, "Cordless Driver 4 & SABO 2" Brochure, 2013: 1 page.

\* cited by examiner

UNIVERSAL CALIBRATION SYSTEM

This application claims the benefit of U.S. Provisional Patent Application No. 62/236,424, filed on Oct. 2, 2015 which is incorporated herein by reference in its entirety and is commonly owned by Stryker Corporation of Kalamazoo, Mich.

TECHNICAL FIELD AND BACKGROUND

The present disclosure generally relates to a control system that is configured to detect when a component is coupled to the control system so that the control system can then calibrate the component for use with the control system.

When a medical device, such as a patient support, is assembled or when it is installed in the field, it may come with standard and optional features. In order for the standard and optional features to be recognized by the medical device control system, and therefore properly operated by the control system, dip switches on the control system are usually manually set. This process tends to be labor-intensive and prone to human error.

SUMMARY OF THE DESCRIPTION

In one embodiment, a medical support control system comprises a medical support having a control system microprocessor. The control system microprocessor is configured for connection with a component for use at the medical support. The control system microprocessor is configured to detect when the component is connected to the control system microprocessor.

In one aspect, the control system microprocessor is configured to calibrate the component once the component is detected as being connected to the control system microprocessor. Further, the control system microprocessor may be further configured to detect proper installation of the component.

In yet a further aspect, the control system microprocessor is configured to run diagnostics on the component.

In one embodiment, the control system microprocessor is configured to calibrate an algorithm of the component.

In any of the above, the medical support control system further comprises a display. The control system is further configured to generate an icon at the display representative of the component.

Optionally, the control system microprocessor is further configured to display a characteristic of the component.

According to any of the above, the component is selected from the group consisting of a battery, a load cell, a motor, a user interface, an electric brake, a treatment device, a pad, and a sleep mode module.

In one embodiment, the component is a battery.

In a further aspect, the control system microprocessor is configured to determine the presence of a battery, and optionally further configured to determine at least one of (1) battery capacity and (2) the battery's time to dead or remaining life.

In yet another aspect, the control system microprocessor detects a current or voltage in the component to thereby detect when the component is connected to the control system microprocessor.

According to any of the above, the medical support comprises a patient support selected from the group consisting of a hospital bed, a medical recliner, a stretcher, a medical chair, an operating room table, and a cot.

In one embodiment, the medical support comprises a medical recliner. Further, the component comprises a component selected from the group consisting of an occupancy detection system, a headwall interface module, and a battery.

In a further aspect, the medical support control system comprises a user input interface in communication with the microprocessor. The user input interface is configured to initiate the detection system detecting when the component is connected to the microprocessor.

In one aspect, the user input interface is located at the medical support.

For example, the user input interface may comprise a user interface selected from the group consisting of a button, a voice recognition system, a proximity sensor, and an RFID tag.

In one aspect, the medical support control system further comprises a display at the medical support, and the user interface comprises a button located at the display.

In another aspect, the user input interface is located remotely from the medical support.

In yet another aspect, the detection system comprises a sensor for detecting when the component is connected to the microprocessor.

In yet another embodiment, the component comprises a load cell. For example, when the load cell is detected by the detection system, the microprocessor is operable to calibrate the load cell, and the microprocessor is operable to zero-out the load cell.

In yet other aspects, the detection system comprises a mechanical detection system, an optical detection system, or an electrical detection system.

In one embodiment, the component comprises a barcode, and the detection system comprises a barcode reader.

In another embodiment, the component comprises an RFID tag, and the detection system comprises an RFID tag reader.

In yet another embodiment, the component comprises a component-based communication device. And, the detection system comprises a medical support-based communication device operable to communicate with the component-based communication device when the component is connected with the microprocessor.

In one aspect, the component based communication device transmits a component identification to the medical support-based communication device. The component parameters are stored in memory, and the microprocessor selects the appropriate parameter or parameters from the component parameters based on the identification.

In another aspect, the component-based communication device comprises a wireless component-based communication device.

In another embodiment, the component comprises memory. The medical support comprises a port in communication with the control system microprocessor such that when the component is mounted in the medical support and the memory is connected to the port, the component is connected to the control system microprocessor.

For example, the memory may comprise a USB device, and the medical support comprises a USB port in communication with the control system microprocessor such that when the component is mounted in the medical support and the USB device is inserted into the USB port, the component is connected to the control system microprocessor.

In other aspects, the memory comprises software associated with the component, and the control system microprocessor is configured to use the software when the memory is connected to the control system microprocessor.

According to yet another embodiment, a medical device control system comprises a medical device, memory, a microprocessor in communication with the memory, and a detection system configured to detect whether a component at the medical device is installed, in need of service, in need of replenishment, or in need of replacement.

In one aspect, the medical device comprises a temperature management apparatus, and the component comprises a coolant.

Alternately, the component comprises a battery.

In any of the above, the component may comprise a DVT component.

In any of the above, the medical device may comprise a patient support, such as a hospital bed.

In a further aspect, the component comprises a mattress. Optionally, the mattress comprises electronics, and the microprocessor calibrates the electronics when the detection system detects the mattress is installed on the patient support.

In another aspect, the component comprises electric brakes. Optionally, the electric brakes have a motor and a brake status switch, and the detection system is operable to detect a position of the brake status switch.

In another embodiment, the patient support comprises a user interface, and the detection system detects characteristics of the user interface. For example, the user interface may comprise a display. The detection system detects display characteristics of the display.

In another aspect, the detection system detects whether the user interface is properly installed.

In another embodiment, the component comprises a motor, and the detection system detects the status of the motor.

In yet another embodiment, the medical device comprises a patient support, and the component comprises a holder for receiving a portable electronic device. The holder has a connection for connecting with the microprocessor when a portable electronic device is positioned in the holder and coupled to the connection so that the portable electronic device is then in communication with the microprocessor.

Optionally, the microprocessor is configured to charge a portable electronic device when positioned in the holder.

According to yet further aspects, the patient support comprises a display, which is in communication with the microprocessor and with the portable electronic device when the portable electronic device is positioned in the holder and coupled to the connection. In this manner, a patient may operate the electronic portable electronic device through the display.

In another embodiment, the microprocessor is configured to activate or deactivate a function based on detecting the presence or absence of the component. For example, the microprocessor may be configured to activate or deactivate a diagnostic capability based on the absence of the component.

In one aspect, the microprocessor is located at the medical device.

Alternately, the microprocessor may be remotely located from the medical device.

According to yet further aspects, the medical device control system comprises a user input interface in communication with the microprocessor. The user input interface is configured to initiate the detection system detecting whether the component of the medical device is installed, in need of service, in need of replenishment, or in need of replacement.

Optionally, the detection system may be configured to auto-detect whether the component of the medical device is installed, in need of service, in need of replenishment, or in need of replacement. For example, the detection may be cyclic or in response to input to the microprocessor.

According to yet another embodiment, a method of managing a medical device comprises the steps of (1) providing a microprocessor associated with the medical device, (2) detecting when a component is installed in the medical device and in communication with the microprocessor, and (3) calibrating the component, either locally at the medical device or remotely from the medical device, when the component is detected as being installed in the medical device and in communication with the microprocessor.

In one aspect, the method further comprises detecting when the component is properly installed in the medical device.

In another aspect, the method further applies diagnostics to the component.

In another aspect, the detecting is in response to a signal being input to the microprocessor.

In yet another aspect, the detecting comprises auto-detecting.

According to yet another aspect, the detecting is in response to a signal generated at the medical device, and optionally in response to a signal generated remotely from the medical device.

In yet another aspect, the detecting comprises detecting a signal from the component.

According to a further aspect, the method comprises displaying an icon at the medical device representative of the component.

Optionally, the displaying additionally or alternatively comprises displaying a characteristic of the component at the medical device.

In yet another aspect, the method further comprises transmitting with the signal a component identification, and selecting an appropriate parameter or parameters based on the component identification.

In another embodiment, a method comprises the steps of (1) associating a microprocessor with a medical device, and (2) detecting whether a component at the medical device is installed, in need of service, in need of replenishment, or in need of replacement.

In one aspect, the method further comprises activating a function based on when a component is detected at the medical device.

In another aspect, the method further comprises deactivating a function based on when a component is not detected at the medical device.

For example, the detecting may comprise: (1) auto detecting, (2) detecting in response to input to the microprocessor, or (3) cyclically detecting.

Before the embodiments of the disclosure are explained in detail, it is to be understood that the disclosure is not limited to the details of operation or to the details of construction and the arrangement of the components set forth in the following description or illustrated in the drawings. The disclosure may be implemented in various other embodiments and is capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the disclosure to any specific order or number of components. Nor should the use of enumeration be construed as excluding from the scope of the disclosure any additional steps or components that might be combined with or into the enumerated steps or components.

DETAILED DESCRIPTION OF THE DRAWINGS

DETAILED DESCRIPTION OF THE PREFERRED EMBODIMENT

Figure 1:
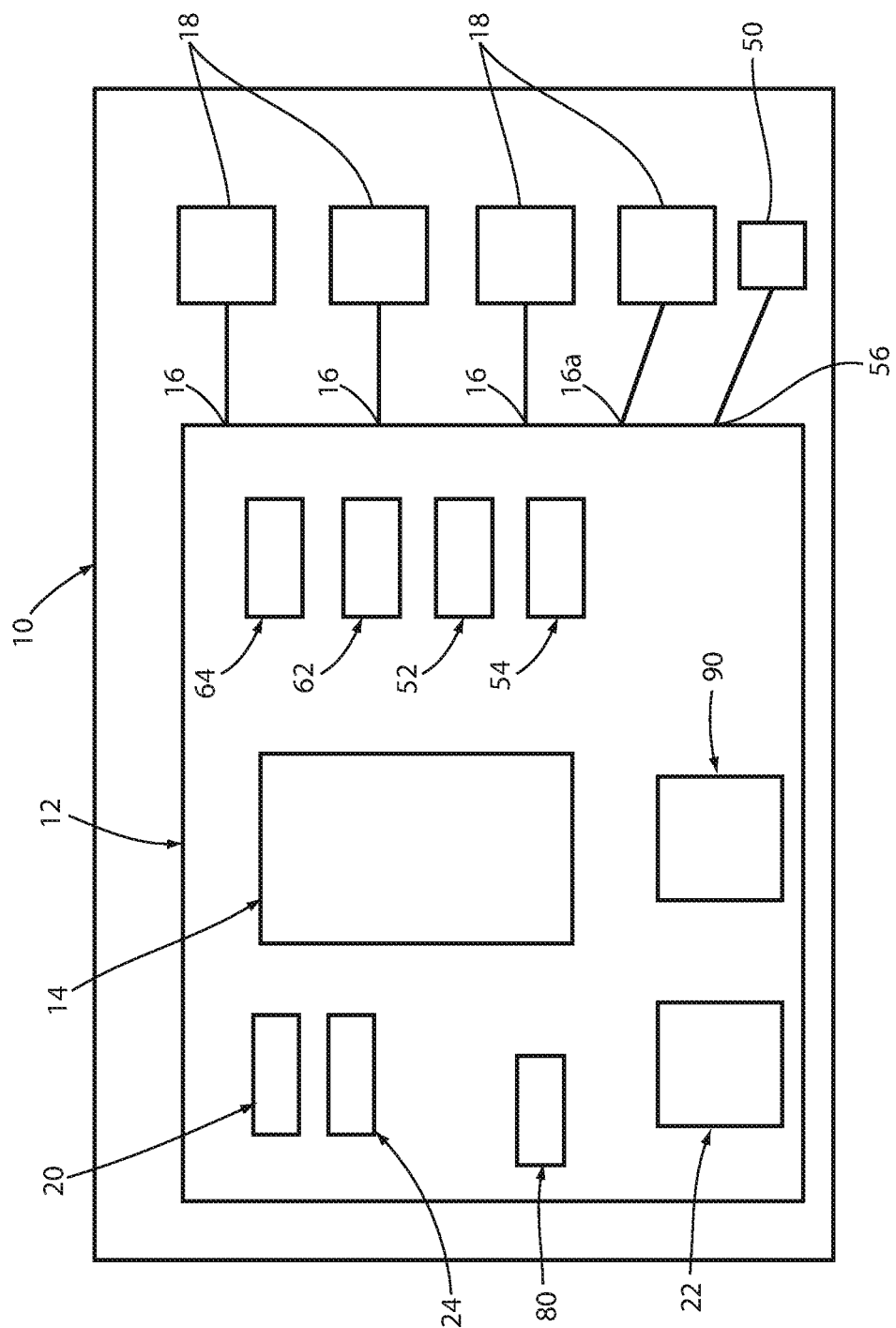
FIG. 1 is a schematic drawing of a universal calibration system.

Referring to FIG. 1, the numeral 10 generally designates a medical device. Medical device 10 may comprise a patient support, including a medical recliner, a hospital bed, a stretcher, or cot, or treatment device, such as a temperature management device. As will be more fully described below, medical device 10 comprises a control system 12 that is configured to detect when a component is connected with the control system 12, such as the control system microprocessor, so that the control system can calibrate the component for use with the medical device. In one embodiment, the control system is configured to detect whether a component is in need of replacement, repair, or replenishment.

Referring again to FIG. 1, control system 12 comprises a microprocessor 14, which may comprise its own memory, and a plurality of connections 16 available for connecting microprocessor 14 with one or more standard or optional components, targets or features 18. Or stated alternatively, control system 12 comprises a plurality of connections with which the one or more standard or optional components may be connected to control system 12 and to microprocessor 14. Further, control system 12 may comprise other microprocessors and/or other programmable electronics that are programmed to carry out the functions described herein, including a graphical user interface for creating and managing images at the display, described below. It will be understood that control system 12 may also comprise other electronic components that are programmed to carry out the functions described herein, or that support the microprocessors and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Further, some of these components may be physically distributed in different positions on medical device 10, or they may reside in a common location on the medical device 10. When physically distributed, the components may communicate using any suitable serial or parallel communication protocol, such as, but not limited to, CAN, LIN, Firewire, I-squared-C, RS-232, RS-485, etc.

It should be understood that the number of connections and components may vary, and the four connections and components illustrated in FIG. 1 are just for illustrative purposes only. Further the term "connections" is used broadly and not intended to be limited to a direct connection, but also include wireless connections. Therefore, control system 12 may also comprise a receiver and a transmitter, or a transceiver 20.

Further, the term "control system" is also used broadly and can simply mean a microprocessor in some cases where additional components are not required or are already part of the microprocessor.

Similarly, the term "component" is not limited to a component part of the medical device and instead can include software, upgrade to component parts, optional features, or consumable components that are used by the medical device itself or in conjunction therewith. Examples of standard or optional components that may be coupled to control system 12 include: batteries; scale systems with pressure sensors, load cells, or strain gauges; user interfaces, such as human machine interfaces (HMI); motors; mattresses; pressure sensing mats; incontinence pads; treatment devices, such as temperature management devices, including pads, DVT pumps and garments, coolants or heaters; vital signs monitoring devices; electric brakes; sleep mode detection modules; an occupancy detection system; a headwall interface module; and software applications.

In one embodiment, the component comprises a subsystem with a subsystem-based communication device. The term "subsystem" refers to a set of elements of a system, which is a system itself. And, the control system comprises a medical device-based communication device operable to communicate with the subsystem-based communication device when the subsystem is connected or in communication with the microprocessor.

In a further embodiment, the subsystem based communication device transmits a subsystem identification to the medical device-based communication device. Subsystem parameters may be stored in memory, and the microprocessor may then select the appropriate parameter or parameters from the subsystem parameters stored in memory to calibrate the subsystem, based on the identification of the subsystem.

An example of subsystem includes a mattress. The mattress may be a mattress of the type disclosed in commonly assigned U.S. patent application Ser. No. 13/836,813 filed Mar. 15, 2013 and Ser. No. 14/308,131 filed Jun. 18, 2014, entitled INFLATABLE MATTRESS AND CONTROL METHODS and PATIENT SUPPORT COVER, respectively, the complete disclosures of both of which are hereby incorporated herein by reference. Such mattresses comprise a plurality of inflatable bladders whose inflation pressure is controllable by one or more controllers contained within the mattress. The mattress may further comprise a plurality of sensors used for detecting information about the status of the mattress, such as, but not limited to, one or more depth sensors, fluid pressure sensors, temperature sensors, patient interface pressures sensors, and/or humidity sensors. Optionally, the medical device comprises a patient support, and the microprocessor calibrates the electronics of the mattress when the detection system detects that the mattress is installed on the patient support.

Another example of a subsystem includes a pressure sensing mat that may be positioned on top of, underneath, or integrated into, a mattress. Such pressure sensing mats are used to detect the interface pressures between the patient and the support surface the patient is positioned on, and can be useful for monitoring such pressures so as to avoid the development, or potential development, of bed sores. A suitable flexible pressure sensing mat is disclosed in commonly assigned PCT patent application serial number PCT/US12/27402, filed Mar. 2, 2012 by Stryker Corporation, and entitled SENSING SYSTEM FOR PATIENT SUPPORTS, the complete disclosure of which is hereby incorporated herein by reference in its entirety. Such a flexible pressure sensing mat may forward pressure information, including but not limited to, a patient interface pressure distribution map, to control system 12, and/or any other information that is detectable by the flexible pressure sensing mat (such as, but not limited to, patient heart rate, patient respiration rate, patient position, patient orientation, patient movement—including patient turns, and other information).

Figure 2:
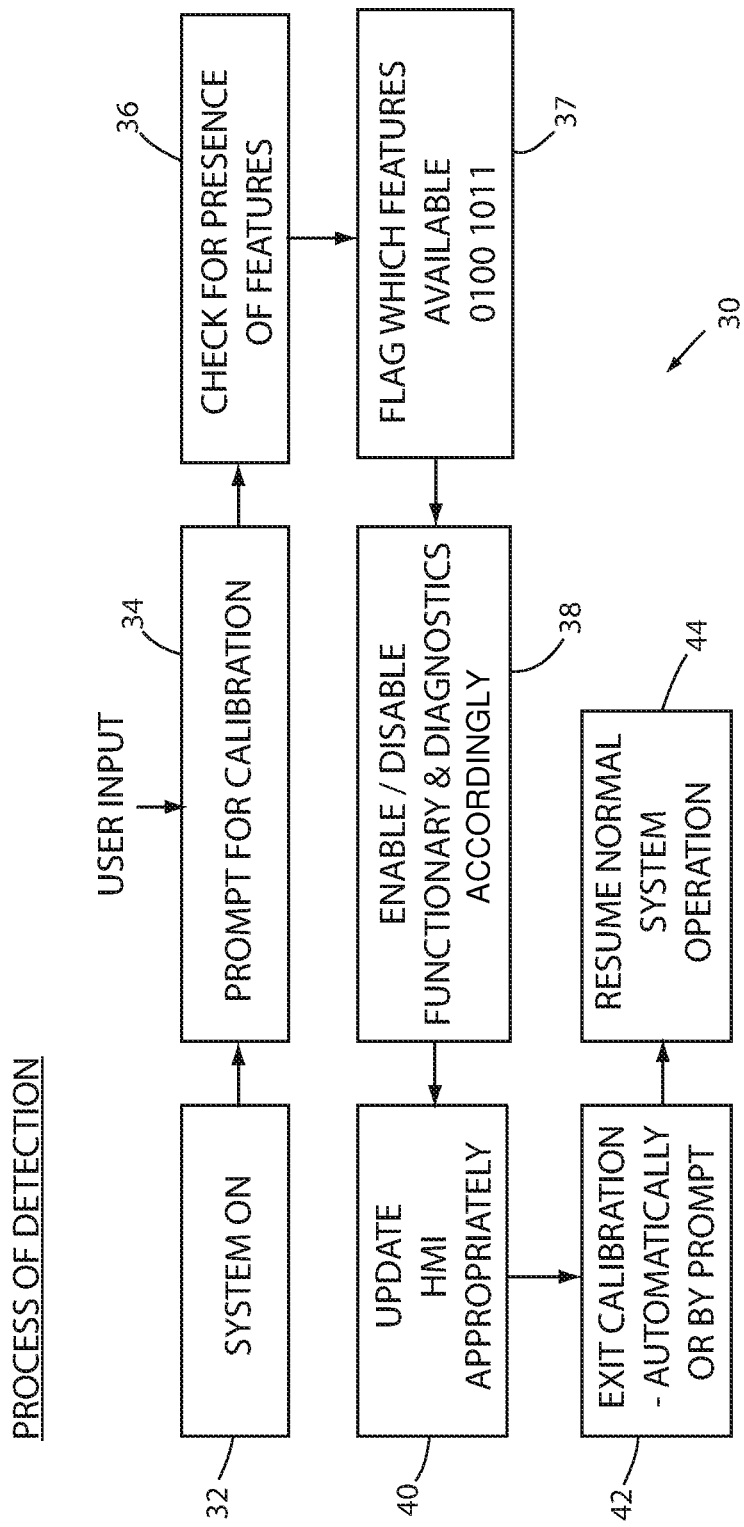
FIG. 2 is a flow chart illustrating a process of calibrating.

Referring now to FIG. 2, the numeral 30 designates one embodiment of a process used by control system 12 for detecting when a component is coupled to control system 12. When control system 12 is powered on (32), either automatically or based on a user input (34), control system 12 checks for the presence of a component (36). This check can be achieved by detecting a current or voltage at any of the connections to the control system 12, including for example, at the inputs to the microprocessor. Alternately, control system 12 may detect whether signal has been received, for example, in the case of a wireless component. After detecting the presence or absence of a component, a flag is set for each detected component and missing component (37). After the flag is set to indicate whether or not the component is connected to the control system, control system 12 thereafter enables/disables the function associated with the component accordingly. Control system 12 further may run the appropriate diagnostics on the component or components that are connected to control system 12 (38).

Optionally, control system 12 comprises one or more user interfaces 22 (FIG. 1), such as an HMI, including a touchscreen, a button, a voice recognition system, a proximity sensor, or an RFID tag. The user input interface is in communication with the microprocessor and is configured to initiate the detection system detecting when the subsystem is connected to the microprocessor. The user input interface may be located at the medical device or may be located remotely, for example, in handheld device or at a nurse call station.

Control system 12 updates user interface 22, according to the presence or lack of a component (40). For example, where control system 12 comprises a user interface in the form of a display, the display may be configured by control system 12 to display an icon or illuminate a button to indicate when a component is coupled to the control system 12. Further, control system 12 may configure the icon or button so that it is operable to control the component. In another embodiment, the detection system detects characteristics of the user interface. For example, the detection system may detect the display characteristics of the display and/or whether the user interface is properly installed.

In some of the embodiments of control system 12, control system 12 comprises a touch screen. The touch screen may be constructed in a number of different ways. For example, the touchscreen may be constructed in a manner disclosed in commonly assigned, U.S. Pat. App. Ser. No. 62/166,354, filed May 26, 2015, by inventors Daniel Brosnan et al. and entitled USER INTERFACES FOR PATIENT CARE DEVICES, the complete disclosure of which is incorporated herein by reference. Alternately, the touchscreen may be constructed in a manner disclosed in commonly assigned, U.S. Pat. App. Ser. No. 62/171,472, filed Jun. 5, 2015, entitled PATIENT SUPPORT APPARATUSES WITH DYNAMIC CONTROL PANELS (P477), the disclosure of which is incorporated herein by reference in its entity. Further, where the medical device comprises a patient support, the display, such as the touchscreen, may be located on the patient support.

After the user interface has been updated, control system 12 exits the calibration process either automatically or based on a prompt from a user (42). Control system 12 then resumes normal system operation (44).

Figure 3:
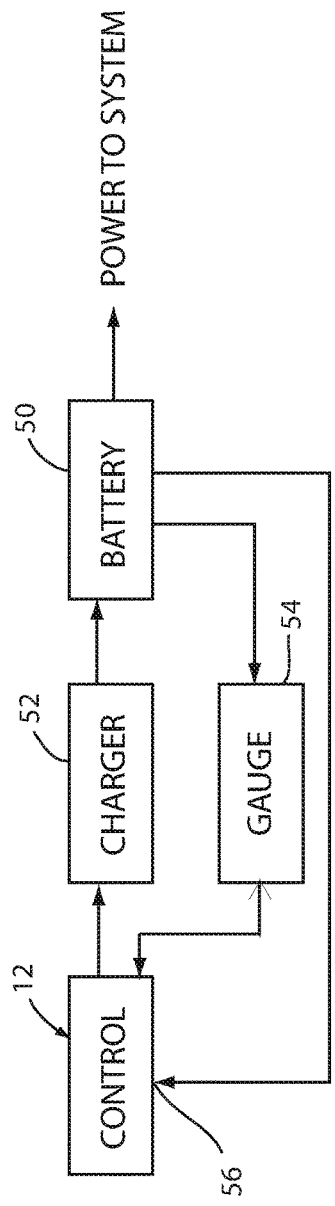
FIG. 3 is a schematic drawing of a calibration system for a battery backup.

In one embodiment, the component comprises a battery 50 (FIG. 3). As best seen in FIGS. 1 and 3, control system 12 comprises a charging circuit or charger 52 and a gauge 54, which is in communication with the battery so that when battery 50 is coupled to the connection 56 at control system 12, control system 12 can detect whether there is a voltage at the connection to detect the presence of battery 50. After control system 12 detects the battery's voltage by gauge 54, control system 12 then enables and energizes the charging circuit 52, which charges the battery. Control system 12 then detects whether there is a current flow to battery 50. If control system 12 detects a voltage in and a current to battery 50, control system 12 configures itself for a battery backup and turns on the battery icon at the user interface. Further, control system 12 configures itself to allow a charge/discharge function. Optionally, control system 12 is further configured to activate a battery diagnostics on the battery.

If control system 12 does not detect either voltage in or current to battery 50, then control system 12 is then configured to disable the battery related functions. For example, battery related functions may include operation of actuators that move, for example, the seat height of a medical recliner, the deck sections of a bed, or operation of a user interface, for example.

In one embodiment, control system 12 may include algorithms to perform diagnostics on the battery. For example, control system 12 may determine the capacity of the battery, remaining life of the battery, or the "golden image", such as disclosed in U.S. Pat. App. Ser. No. 62/160,155, filed May 12, 2015 (P476), which is commonly owned by Stryker Corporation of Kalamazoo, Mich. and incorporated by reference in its entirety herein.

In another embodiment, the battery may be a "subsystem" in that it may comprise memory and a battery based communication device to communicate information about the battery to the control system.

Other subsystems may include, as noted above, a headwall interface module, an occupancy detection system or other modules or systems.

Figure 4:
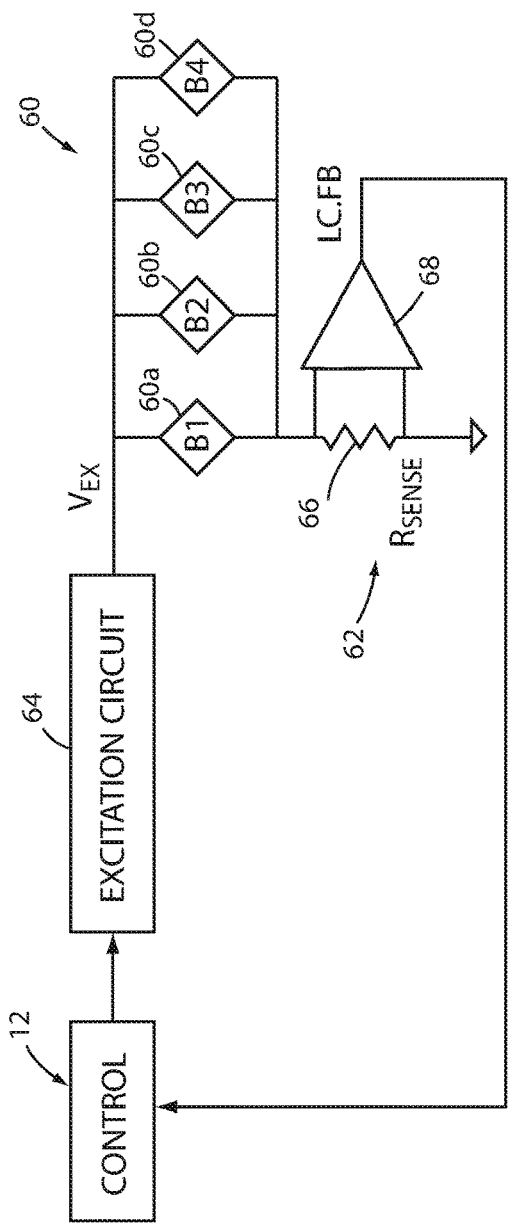
FIG. 4 is a schematic drawing of a load cell detection system.

In one embodiment, illustrated in FIG. 4, the component is a scale system 60. For example, scale system 60 may comprise load cells, pressure sensors, or strain gauges to measure the weight of a patient, for example. In the illustrated embodiment, scale system 60 comprises a plurality of load cells 60a, 60b, 60c, and 60d, which are connected in parallel. In order to detect load cells 60a-d, control system 12 comprises a sensor 62, which detects the current flow through the load cells. In order to excite load cells 60a-d, control system 12 comprises an excitation circuit 64, which applies a voltage across the load cells, which then generate a current output at sensor 62. For example, sensor 62 may comprise a resistor 66 in series with the output of load cells 60a-d and in parallel with an amplifier 68. In this manner, when a current flows through the resistor from the load cells, the amplifier will be turned on. The amplifier's output is input to the microprocessor 14 of control system 12, which when turned on signals presence of the load cells to the control system 12. The input to the amplifier may be current or voltage, and the output of the amplifier may be current or voltage. Similar to the previous embodiments, when control system 12 detects the presence or lack of the load cells, control system 12 sets a flag to indicate their presence or lack thereof.

Once the flag is set to indicate the load cells are present, control system 12 may run a calibration routine on the load cells. For example, using the excitation current, control system 12 can zero-out the load cells and determine the state of the load cells and, further, indicate, for example, when the load cells need to be replaced or determine the expected remaining life of load cells. For example of a suitable diagnostics that can be run on the load cells by control system 12, reference is made to the U.S. Pat. App. Ser. No. 62/186,464 entitled PERSON SUPPORT APPARATUSES WITH LOAD CELLS, filed on Jun. 30, 2015 (P 482), which is commonly owned by Stryker Corporation of Kalamazoo, Mich. and incorporated by reference herein in its entirety.

Figure 4A:
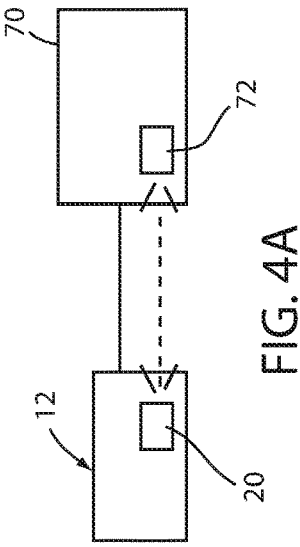
FIG. 4A is a schematic drawing of a first embodiment of a target detection system.

In one embodiment illustrated in FIG. 4A, the component may comprise a motor 70. Control system 12 may detect motor 70 by checking resistance at the motor connection. If the resistance at the motor connection is above a preselected threshold, control system 12 flags that a motor is coupled to the control system 12.

Optionally, motor 70 comprises a serial number, which may be stored on a tag 72, such as an RFID tag. As noted above, control system 12 may comprise a transmitter and receiver or transceiver 20, which is configured to selectively generate a signal to excite the tag. Referring to FIG. 4A, in response to the signal from the transceiver, the tag generates a signal with the serial number, so that when control system 12 receives the signal from the motor's tag, control system 12 can use the serial number to determine the parameters of the motor. For example, control system 12 may comprise memory, which is either part of the microprocessor 14 or a separate memory 24 (FIG. 1), which stores a lookup table or database. The lookup table or database includes parameters associated with the serial number so that control system 12 can access the parameters associated with the motor for calibration and/or for the settings of the motor. For example, the parameters may include the status of or information about the motor. Optionally, the motor may comprise memory and have a battery-based communication device that transmits information stored in its memory about the battery to control system 12.

When the medical device comprises a patient support, such as a hospital bed or medical recliner, control system 12 using the parameters saved in the memory can then drive the motor to move one or more components, such as a deck section or a deck frame, to adjust the configuration or height of the patient support to a predefined configuration or height. Thereafter, control system 12 may then calibrate the patient support configuration.

Figure 4B:
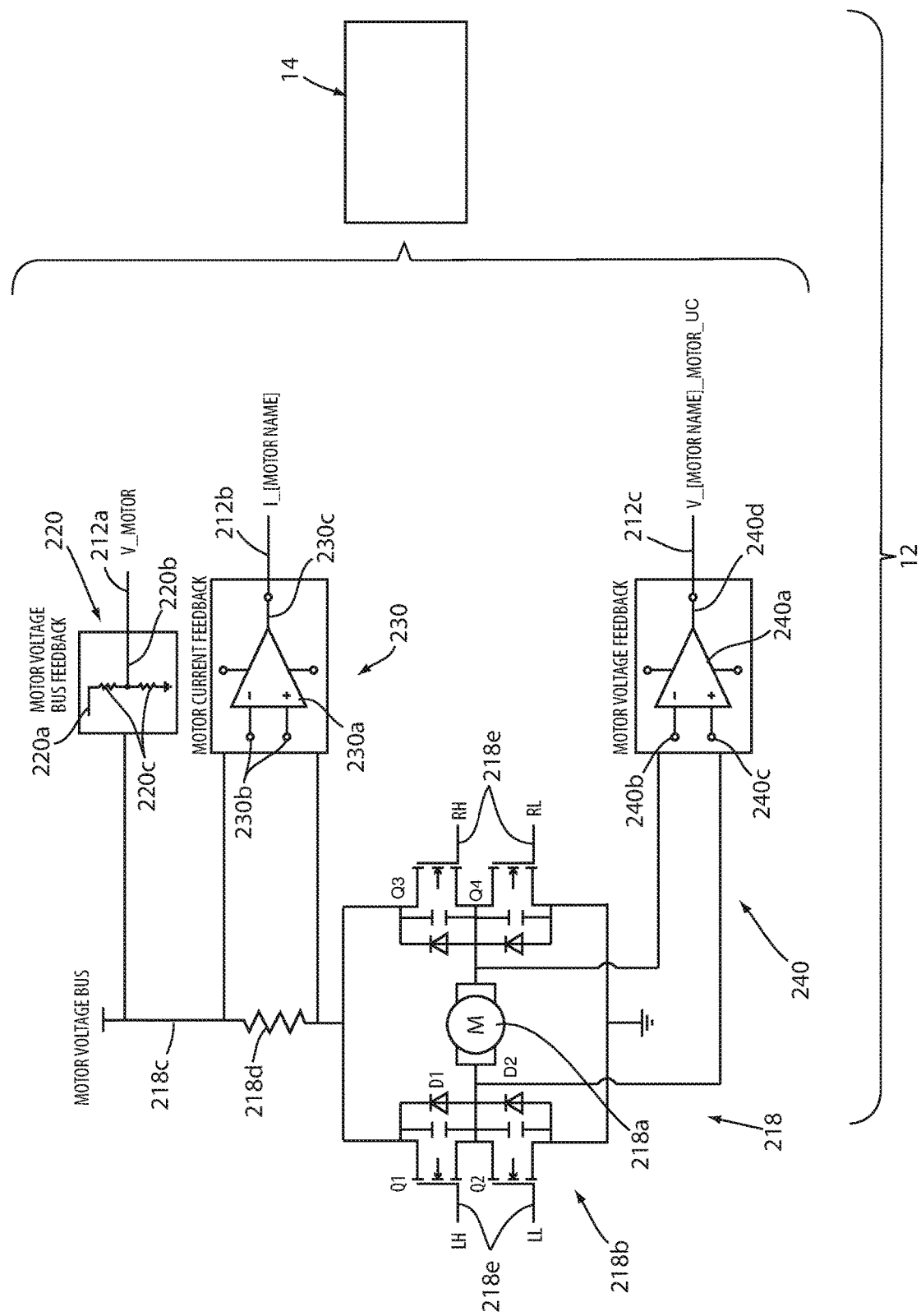
FIG. 4B is a schematic drawing of a motor and motor drive system and diagnostic system therefor.

Referring to FIG. 4B, the numeral 218 generally designates another embodiment of a component that can be diagnosed and/or calibrated by control system 12. In the illustrated embodiment, the component 218 comprises a motor and motor drive system, such as a motor and motor drive system of a patient support apparatus, such as a hospital bed or a medical recliner. In the illustrated embodiment, motor and motor drive system 218 is a motor and motor drive system for a patient support apparatus and includes a motor 218a and a motor driver circuit 218b, which is configured to drive motor 218a.

Motor drive circuit 218b comprises an H-Bridge driver with four FETS 218e (FIB. 4B), with two low side FETs and two high side FETs, each with a corresponding catch diode. As noted above, control system 12 may be integrated into the medical device or may comprise a control system that simply communicates with the medical device. In the illustrated embodiment, the control system is incorporated into the patient support apparatus and may form the main control system of the patient support apparatus to control various components, such as actuators, for example for raising the patient support surface, articulating the patient support surface, actuating brakes, or controlling and/or being responsive to a display at the patient support apparatus.

In the illustrated embodiment, microprocessor 14 is in communication with motor and motor drive system 218, which provides inputs 212a, 212b, 212c from motor and motor drive system 218 to microprocessor 14 for diagnosing and/or calibrating motor 218a and motor drive circuit 218b of system 218, and optionally other in line components noted below.

For example referring again to FIG. 4B, control system 12 includes a motor voltage bus feedback circuit 220, which is electrically coupled to the motor voltage bus 218c. Motor voltage bus feedback circuit 220 comprises a voltage divider with a voltage input 220a that is electrically coupled to motor voltage bus 218c and a voltage output 220b, which provides input 212a to microprocessor 14 of control system 12. The voltage divider may be formed, for example, by two resistors 220c.

Control system 12 further includes a motor current feedback circuit 230 that includes an operational amplifier 230a, whose inputs 230b are coupled to motor voltage bus 218c on either side of a resistor 218d. The output 230c of amplifier 230a also provides input 212b to microprocessor 14.

In addition, control system 12 includes a motor voltage feedback circuit 240 that includes an operational amplifier 240a whose inputs 240b, 240c are electrically coupled the low side and the high side, respectively, of the motor 218a. The output 240d of amplifier 240a also provides input 212c to microprocessor 14 of control system 12.

Control system 12 may run one or more diagnostics test on motor and motor drive system 218 based on one or more of these inputs, and other input noted below. For example, using the parameter(s) stored in or transmitted to control system 12, control system 12 may run diagnostics tests, including periodic diagnostics tests, on the motor based on or in response to a user input at the user interface.

Optionally, in addition to diagnosing motor 218*a* and motor drive circuit 218*b*, control system 12 may also diagnose other in line components, such as other circuits associated with motor 218*a* and motor drive circuit 218*b*, such as a power gating circuit and a pa breaking circuit. Suitable embodiments of a suitable power gating circuit and of a passive breaking circuit are illustrated in FIG. 4C.

Figure 4C:
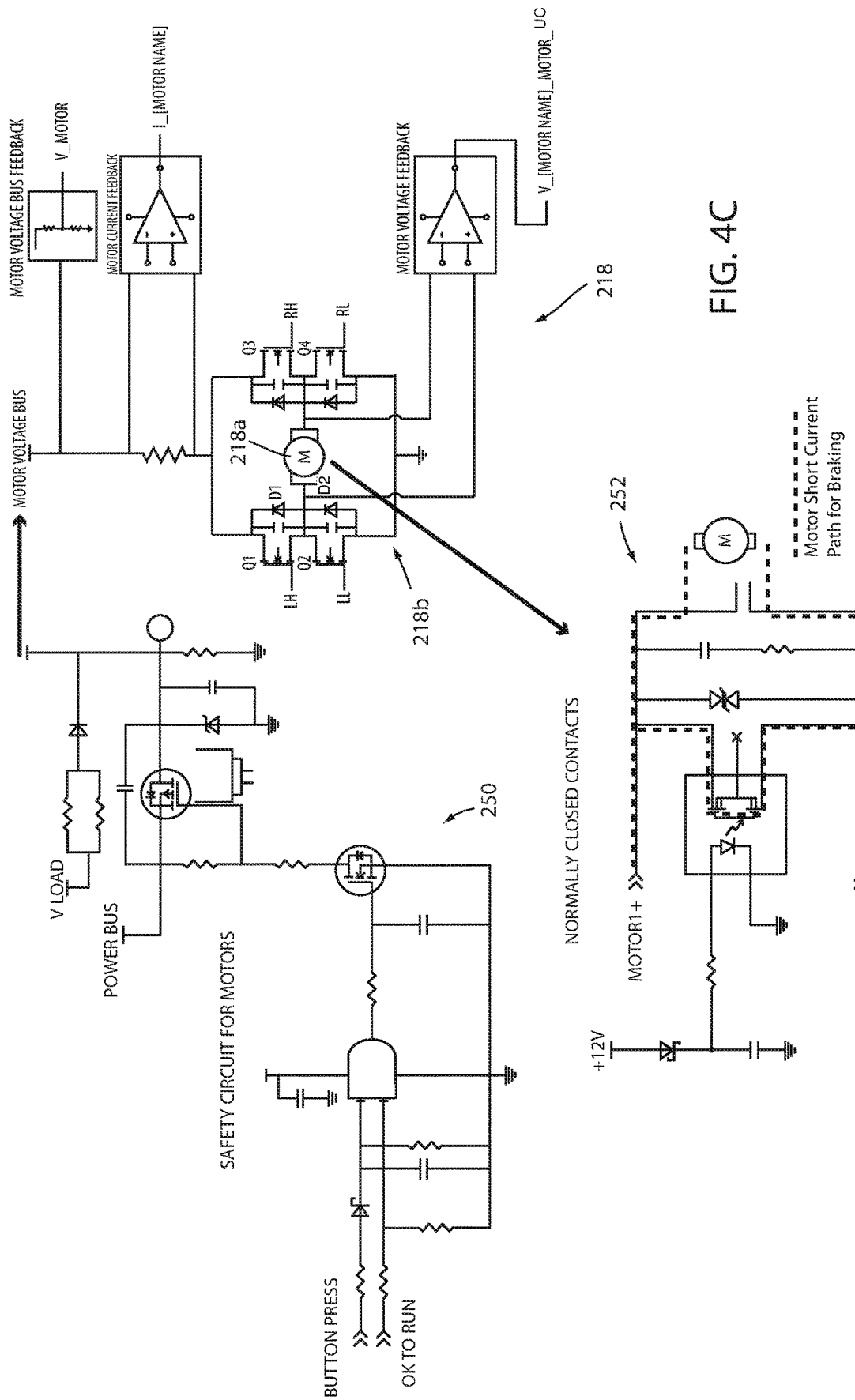
FIG. 4C is a schematic drawing of the motor and motor drive system circuits.

Referring to FIG. 4C, in addition to motor drive circuit 218*b*, motor and motor drive system 218 includes a power gating circuit 250. Power gating circuit 250 controls the maximum allowable power supply drive circuit 218*b* can supply to motor 218*a* and its associated circuits. Passive braking circuit 252 works independent of power gating circuit 250 and motor drive system 218 but is in electrical connection with the motor 218*a* at all times. A control device, such as a user button, provides a control al to the gate terminal of the power gating circuit transistors to control whether the transistors are on or off. When the power gating circuit transistors are on, current passes between the power supply and the motor (and its associated circuits) to power up the motor. When the power gating transistors are off, the manor is decoupled from the power supply, and the motor is no longer powered. By using the power gating circuit to cut off the power supply to the motor, power consumption can be reduced and, rover, the motor can be protected from possible power overloads.

Referring again to FIG. 4C, motor and motor drive system 218 may include a passive breaking circuit 252 that includes a normally closed relay that when opened provides an electrical short circuit across the motor when the system is unpowered, such as described in a commonly assigned U.S. patent application Ser. No. 14/838,693 filed Aug. 28, 2015 titled PERSON SUPPORT APPARATUS WITH ACTUATOR BRAKE CONTROL. When the system is powered, the passive brake will maintain in the OPEN condition, effectively eliminating any passive braking capacity. As will be more fully described below in reference to FIG. 4D, in addition to receiving input from motor bus feedback 218*c* and the high and low sides of motor 218*a*, microprocessor 14 of control system 12 may provide input to power gating circuit 250 and passive breaking circuit 252.

Figure 4D:
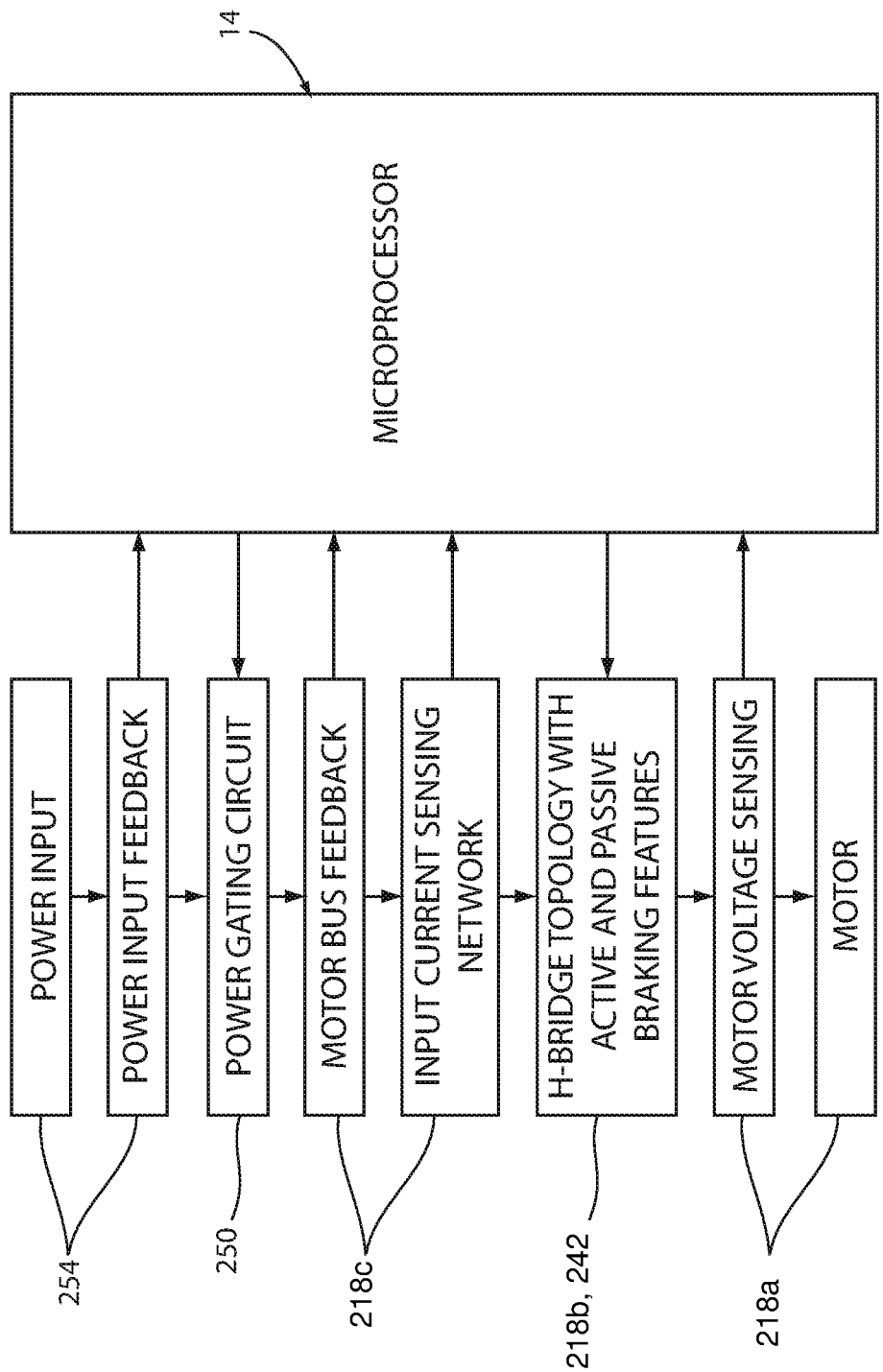
FIG. 4D is a schematic drawing of the diagnostic system for the motor and motor drive system.

Referring to FIG. 4D, microcontroller 14 is in communication with the power input 254, power gating circuit 250, motor bus feedback 218*c*, and motor 218*a*. Further, microcontroller 14 is in communication with the motor drive circuit 218*b*. The passive brake is not in communication with the micro controller 14 specifically so that it cannot control its behavior. The passive brake is controlled exclusively by the presence or absence of system input power.

Figure 4E:
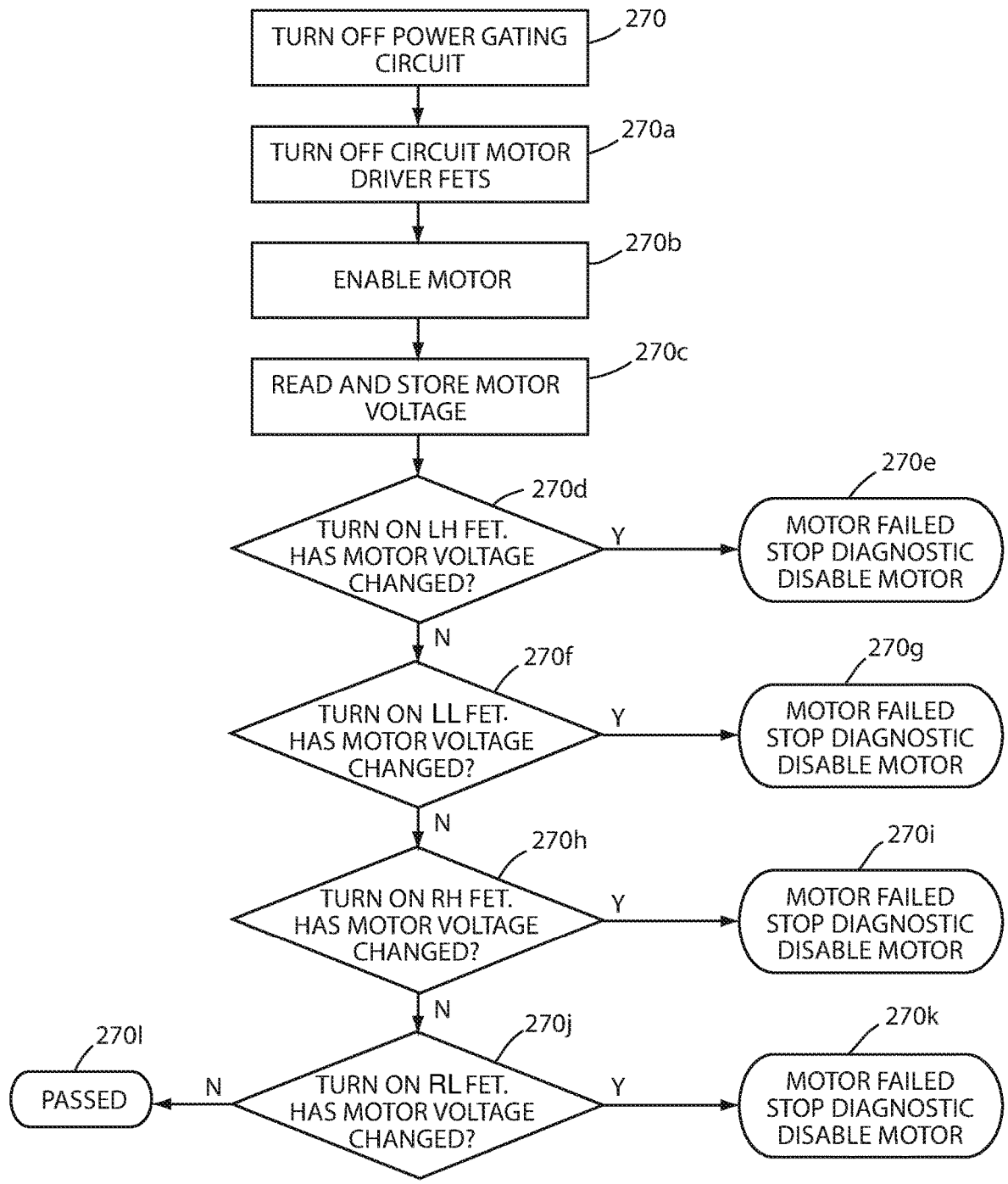
FIG. 4E is a flow chart of a motor diagnostic test steps.

To diagnose the motor and the motor drive circuit, in one diagnostic test, the software on microcontroller 14 turns on each FET 218*e* (FIG. 4B) of the motor drive circuit 218*b* individually and checks the input from the motor to determine whether the motor passes the test or not. Referring to FIG. 4E, microprocessor 14 first turns off the power gating circuit 250 (270). Microprocessor 14 then turns off the motor drive circuit FETS 218*e* (270*a*), and then enables motor 281*a* (270*b*). Microprocessor 14 then reads and stores the voltage of motor 218*a* (270*c*).

The next step is for the microprocessor 14 to turn on the FETS 218*e* one by one and read the voltage of the motor 218*a* when each FET is turned on. For example, microprocessor 14 may first turn on the left high FET (270*d*) and then read the motor voltage. If the motor voltage has changed (more than 5% of the first voltage reading), then microprocessor 14 will stop the diagnosis and disable the motor as this represent a motor failure (270*e*). If the motor voltage has not changed (it is within 5% of the first voltage reading), then the microprocessor will continue to check the other FETS.

For example, microprocessor 14 may then turn on the left low FET (270*f*) and read the motor voltage again. If the motor voltage has changed (more than 5% of first voltage reading), then microprocessor 14 will stop the diagnosis and disable the motor (270*g*) as this represents a motor failure. If the motor voltage has not changed (it is within 5% of first voltage reading), then the microprocessor will continue to check the other FETS.

For example, microprocessor 14 may then turn on the right high FET (270*h*) and read the motor voltage again. If the motor voltage has changed (more than 5% of first voltage reading), then microprocessor 14 will stop the diagnosis and disable the motor (270*i*), as this again represents a motor failure. If the motor voltage has not changed (it is within 5% of first voltage reading), then the microprocessor will continue to check the other FETS.

The microprocessor 14 will then turn on the last FET, for example, in this sequence the right low FET (270*j*) and read the motor voltage again. If the motor voltage has changed (more than 5% of first voltage reading), then microprocessor 14 will stop the diagnosis and disable the motor (270*k*) as this again represents a motor failure. If the motor voltage has not changed (it is within 5% of first voltage reading), then the microprocessor will stop the tests for that motor (270*l*), and optionally indicate that the motor has passed, and then repeat the above steps for the other motor.

For this diagnostic test, microprocessor 14 may use following software:

Shorted H-Bridge Single FET Test:
1) OK_TO_RUN=OFF
2) LH, LL, RH, RL=0
3) [motor name]_MOTOR_ENABLE=ON
4) Check V_MOTOR VOLTAGE and store it
5) LH=ON, Check that V_MOTOR is unchanged (within 5% of original reading)
   a. If YES→System OK, Proceed
   a. If NO→TEST FAILED, STOP DIAGNOSTIC, DISALLOW MOTION
6) LL=ON, Check that V_MOTOR is unchanged (within 5% of original reading)
   a. If YES→System OK, Proceed
   b. If NO→TEST FAILED, STOP DIAGNOSTIC, DISALLOW MOTION
7) RH=ON, Check that V_MOTOR is unchanged (within 5% of original reading)
   a. If YES→System OK, Proceed
   c. If NO→TEST FAILED, STOP DIAGNOSTIC, DISALLOW MOTION
8) RL=ON, Check that V_MOTOR is unchanged (within 5% of original reading)
   a. If YES→System OK, Proceed
   d. If NO→TEST FAILED, STOP DIAGNOSTIC, DISALLOW MOTION
9) TEST COMPLETE→PASSED By turning on each FET individually, the control system 12 can check that there is nothing dragging the motor bus voltage down. In normal operation a single FET being turned on would not cause the system to draw any current from the bus unless there is an adjacent FET on the same half H-Bridge that is shorted (i.e. the failure condition). In that case, a momentary current limited shot-thru would occur and discharge the voltage bus bulk capacitance.

In another or a second diagnostic routine to test for motor and motor drive system 218, microprocessor 14 activates each full bridge and checks that the voltage bus doesn't collapse to zero and that the voltage bus doesn't rise in voltage. If the voltage bus collapses to zero, then the motor has a shorted output. If the voltage bus rises in voltage, then there is an open FET.

This diagnostic test may be repeated for each motor on a medical device.

Figure 4F:
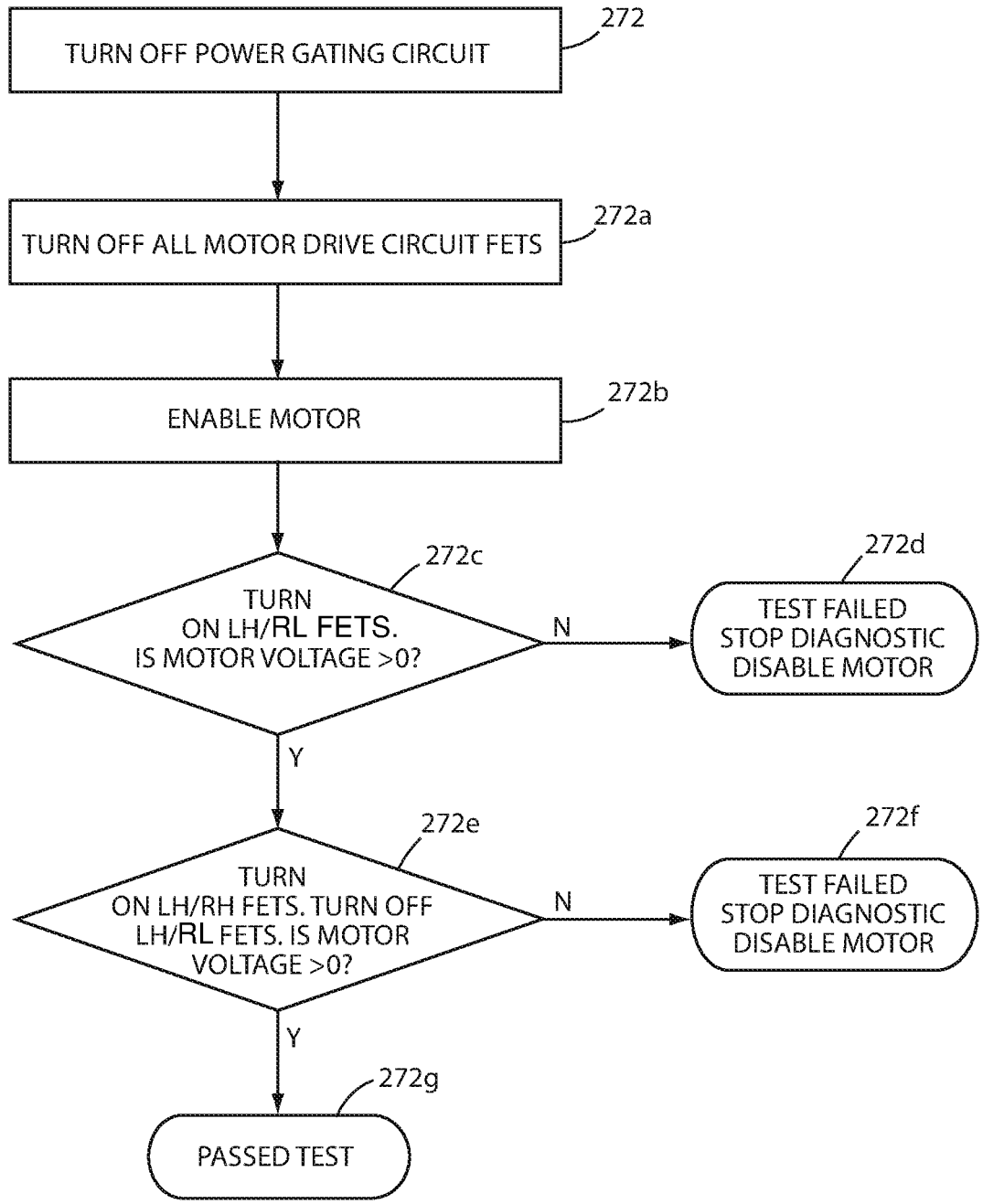
FIG. 4F is a flow chart of a second motor diagnostic test steps.

In the second diagnostic test, the software on microcontroller 14 turns on FET 218e in pairs and checks the input from the motor to determine whether the motor passes the test or not. Referring to FIG. 4F, microprocessor 14 first turns off the power gating circuit 250 (272). Microprocessor 14 then turns off the motor drive circuit FETS 218e (272a), and then enables motor 281a (272b).

The next step is for the microprocessor 14 to turn on the FETS 218e in pairs and to read the voltage at the motor 218a. For example, microprocessor 14 may first turn on the left high and right low FETs (272c) and then read the motor voltage. If the motor voltage is greater than zero (shorted output test) and the motor voltage does not increase over time (open FET test), then the microprocessor will continue to check the other FET pair. If either the motor voltage is not greater than zero or the motor voltage changes over time, then microprocessor 14 will stop the diagnosis and disable the motor as this represents a motor failure (272d).

If the motor passed the first check, microprocessor 14 then turns on the left low and right high FETs (272e) and reads the motor voltage again. If the motor voltage is greater than zero (shorted output test) and the motor voltage does not increase over time (open FET test), then the microprocessor will stop the test for that motor (272g), and optionally indicate that the motor has passed, and then repeat the above steps for the other motor (s). If either the motor voltage is not greater than zero or the motor voltage increases over time, then microprocessor 14 will stop the diagnosis and disable the motor as this represents a motor failure (272f).

In this second diagnostic test, microprocessor 14 of control system 12 may use the following software to diagnose each motor:

Shorted Motor, Shunt Relay, Open FET Test:
1) OK_TO_RUN=OFF
2) ALL MOTORS LH, LL, RH, RL=0
3) [motor name]_MOTOR_ENABLE=ON
4) LH/RL=ON, Check that V_MOTOR>0V (Shorted Output Test) and V_MOTOR DOES NOT INCREASE OVER TIME (open FET Test)
a. If YES→System OK, Proceed
b. If NO→TEST FAILED, STOP DIAGNOSTIC, DIS-ALLOW MOTION
5) LL/RH=ON THEN LH/RL=OFF, Check that V_MOTOR>0V (Shorted Output Test) and V_MOTOR DOES NOT INCREASE OVER TIME (open FET Test)
a. If YES→System OK, Proceed
b. If NO→TEST FAILED, STOP DIAGNOSTIC, DIS-ALLOW MOTION This is repeated for all motors ensuring that each motor is always engaged to keep the bus collapsed. As noted, this diagnostic test or routine turns on the FETs in a paired sequence such that the motor is engaged with a current limited voltage supply in each of its operating scenarios of each motor. For example for a medical device, such as a patient support apparatus, including a hospital bed or a recliner chair, this may include extending or retracting a portion of the patient support apparatus or raising or lowering the patient support surface of the patient support apparatus or actuating a brake.

In the case that one half h-bridge's high side FET is on, and the other half h-bridge's low side FET is on (i.e. a motor directional command) one would expect that the magnitude of applied voltage to the motor is equivalent to the bus. In the case the motor/shunt relay/harnessing is shorted one would not see any voltage potential across the motor—decaying the bus (i.e. the fault condition).

This single test sequence can look for all of the above.

Figure 4G:
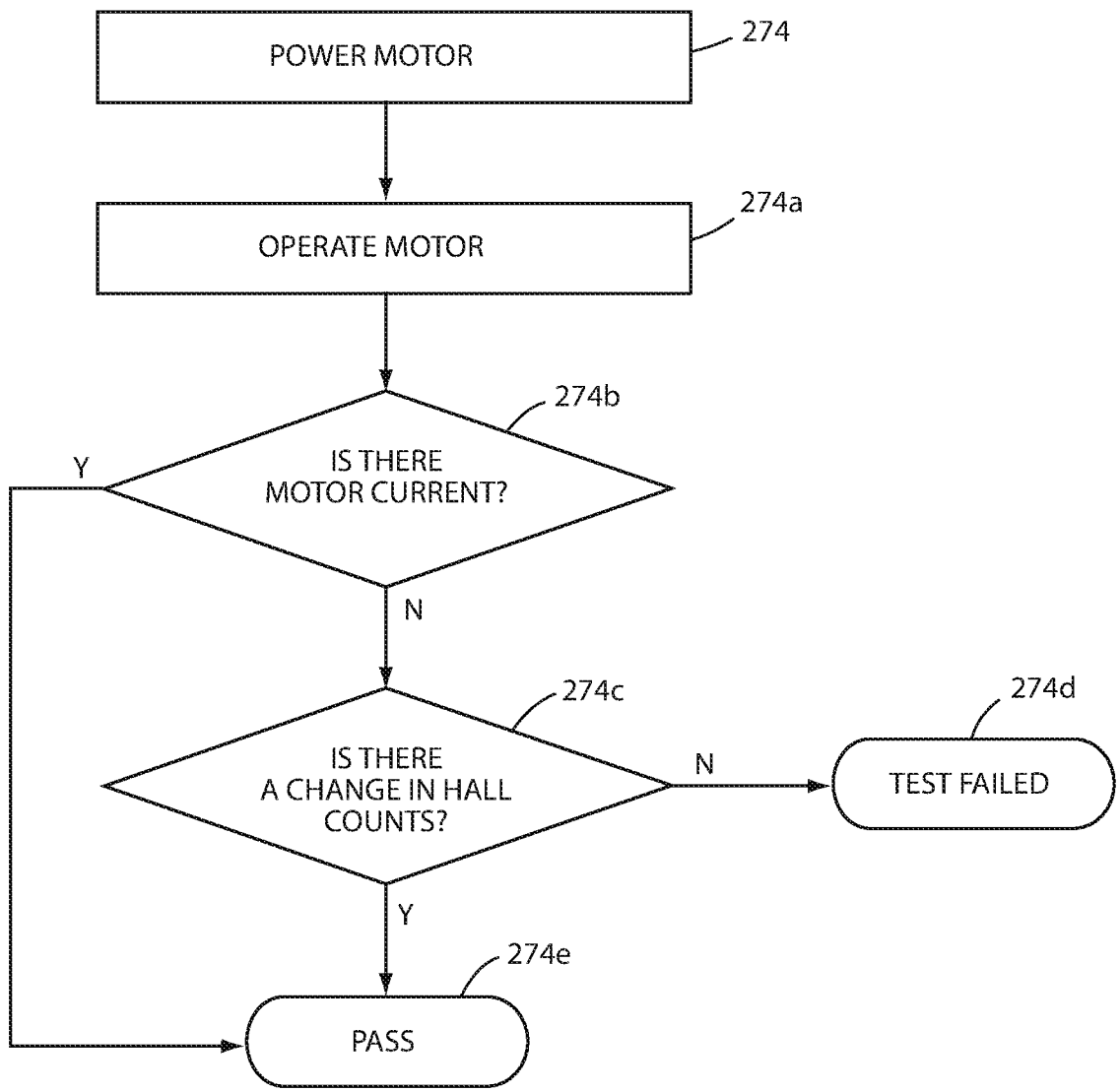
FIG. 4G is a flow chart of a third motor diagnostic test steps.

Referring to FIG. 4G, in a third diagnostic test, the software on microcontroller 14 allows power to the motor (274) and operates/controls motor (274a). For example, the motor can be powered and then driven in the extend direction. The next step is for the microprocessor 14 to check if there is any motor current detected (274b) over a defined period of time, such as 0.1 seconds. Microprocessor 14 also checks to see if there is a change in Hall counts (which detect movements) (274c). If there is no motor current observed and no changes in Hall counts, then the microprocessor will stop the test and disable the motor as this represents that the motor failed the test (274d) and there is a motor failure. If the microprocessor detects motor current or detects a change in Hall counts, then the microprocessor will stop the test for that motor, which indicates that the motor passed the test (274e), and then repeats the above steps for the other motor or motors.

In this third diagnostic test, microprocessor 14 of control system 12 may use the following software to diagnose each motor:

Open Circuit Motor Test:
When motor is commanded to run both of the following must be true over a 0.1 s period in order to register a failure:
NO Motor Current observed on I_[motor name]
NO Hall Counts Change
If both of the above are TRUE, FAILED, DIS-ALLOW MOTION In order to test that the motor, or in-line components, are not open circuited voltage must be applied to the H-Bridge output and hence current is created. Because it is undesirable to have the apparatus potentially move when current passes through the motor it is not appropriate to carry this procedure as part of a pre-run-time diagnostic test like the other diagnostic tests previously described above. Here, the motor will be energized in run time (while the motor is operating) and in the case that there is no current or Hall Count changes (detected movement) it can be assumed that the motor is open circuited and therefore fails the test.

Optionally, in the situation where there is a system issue (wiring short, mechanical interference) where no HALL counts are registered but there is current detected, control system 12 may be configured to disable the motor to stop any motion, but this may not need be part of the drive diagnostics, rather another run time check and interrupt.

Figure 6:
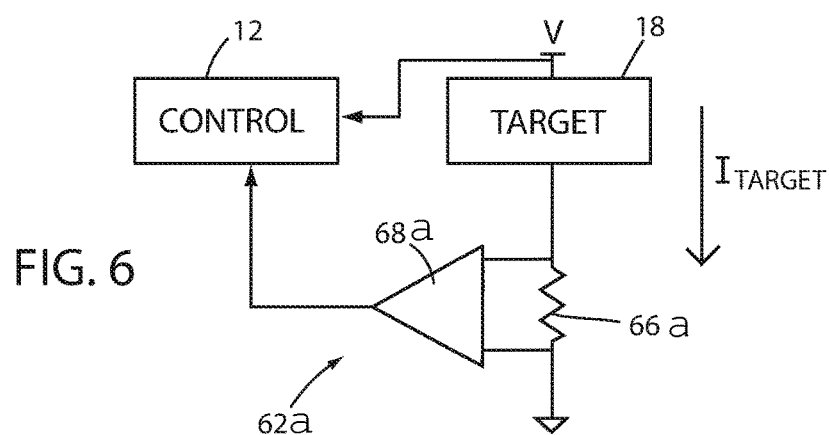
FIG. 6 is a schematic drawing of a second embodiment of a target detection system.

Several other methods of detecting the presence of a component may be used. As noted above, control system 12 may detect a voltage or a current at a specified connection for given component to determine whether the component is connected to the control system. For example referring to FIG. 6, similar to as described in reference to the load cells in FIG. 4, control system 12 may comprise a sensor 62a at one or more of its connections (16, FIG. 1) for detecting a target or component 18. In the illustrated embodiment, sensor 62a is configured to sense current through component 18 to detect the presence of the component. Sensor 62a comprises a resistor 66a that connects to the component output. The resistor 66a is connected in parallel with an amplifier 68a, which is turned on when sufficient current flows through the resistor from the component. The amplifier's output provides input to the microprocessor to indicate the presence of the component. When the amplifier is not turned on, the input at the microprocessor is zero, which indicates the absence of the component. Alternately, the resistor may be coupled in parallel to the component so that it can generate a voltage when current flows through the resistor and then turn on the amplifier in a similar manner as described above to indicate the presence of the component.

Figure 5:
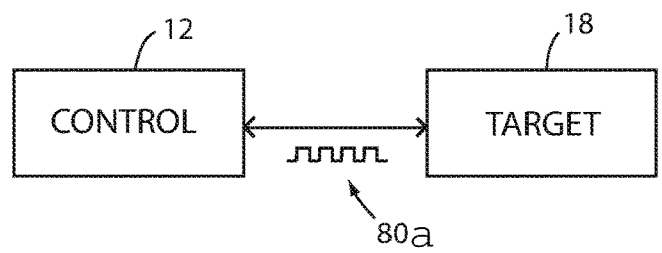
FIG. 5 is a schematic drawing of a first embodiment of a target detection system.

Alternately, for example, control system 12 may comprise a communication device 80 (FIG. 1) for communicating with the component 18. For example, a suitable communication device may be an Ethernet, RS-485, or I2C device or as noted above a wireless device, such as a transmitter or a transceiver that generates a wireless signal 80a (FIG. 5) to allow either one way or two way communication with the target or component 18. Similarly, as noted above, the component may include its own memory and communication device, which can send a signal to control system 12 indicating identification of the component, including information about the component, such as the component's parameters. For example, a suitable communication system between the control system and the component is disclosed in U.S. patent application Ser. No. 14/622,221, entitled COMMUNICATION METHODS FOR PATIENT HANDLING DEVICES, filed Feb. 13, 2015 (P432A), which is commonly owned by Stryker Corporation of Kalamazoo, Mich. and which is incorporated by reference herein in its entirety. In this manner, the control system can directly communicate with the component to determine when the component is connected with the control system, and thereafter calibrate the component and optionally adjust the settings of the component as needed.

In yet another embodiment, control system 12 may comprise a USB port 16a at one of its connections or the component may have a USB port. For example, the USB port may be in communication with the memory of the microprocessor 14 or separate memory 24 of control system 12 and allow a component with a USB device to connect to the USB port and upload information about the component to the control system, e.g. to the memory of the microprocessor 14 or memory 24, which allows control system 12 to calibrate the component based on the uploaded information. Further, when the USB device of the component is inserted into the USB port, the component is connected to and may communicate with the control system. The information may include, for example, settings for the component, the identity of the component, and treatment protocols or plans using the component.

Figure 7:
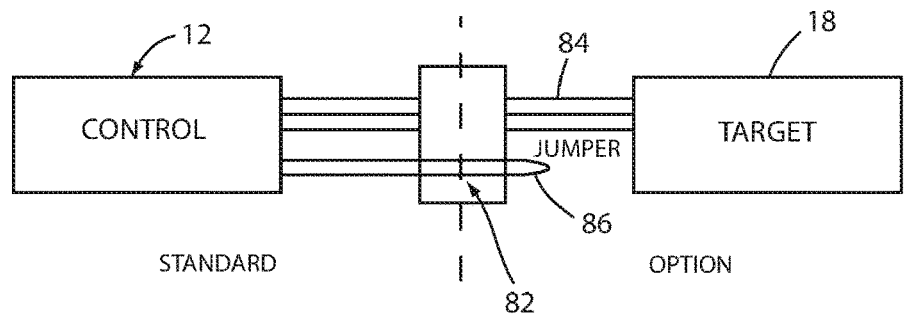
FIG. 7 is a schematic drawing of a third embodiment of a target detection system.

Referring to FIG. 7, control system 12 may detect the presence of a component using a jumper 86. As best seen in FIG. 7, the component may comprise a connector 82 with a plurality of pins 84 for connecting to corresponding sockets on the microprocessor of control system 12 and a jumper 86, which couples two of the inputs of the microprocessor together, which provides an indication to control system 12 that the component is connected to control system 12.

Figure 8:
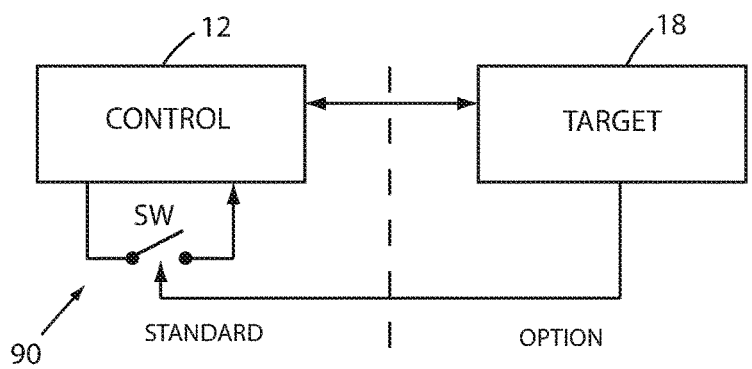
FIG. 8 is a schematic drawing of a fourth embodiment of a target detection system.

Alternately, referring to FIG. 8, control system 12 may also use a switch 90 to detect the presence of the component. Switch 90 is in series with the component and may comprise an electronically controlled switch (such as, for example, a Metal Oxide Semiconducting Field Effect Transistor: MOSFET), that is opened and closed by the component. The switch provides input to the microprocessor of control system 12 and indicates to the microprocessor that the component is connected to control system 12 when the switch is closed, for example.

Figure 9:
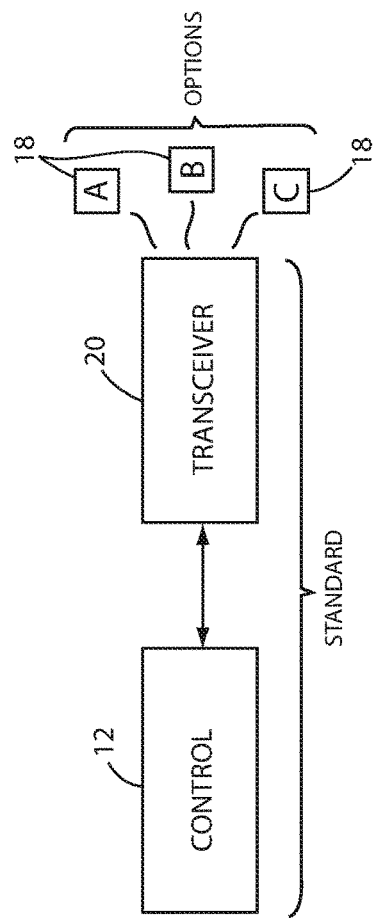
FIG. 9 is a schematic drawing of a fifth embodiment of a target detection system.

In one embodiment, referring to FIGS. 1 and 9, control system 12 comprises a transceiver 20 that communicates with the component or components. For example, transceiver 20 may comprise WiFi communications, Bluetooth and/or ZigBee communications, or other protocols, and may comprise a near field communications transceiver. Such a near field communications transceiver can be used for establishing an association between the medical device 10 and the component, which association is then used by the control system to indicate that the component is present and connected to the control system. Once the association is established, the control system can then run the appropriate diagnostics on the component to calibrate the component and/or control the settings of the component so that the settings are suitable for the specific application with the medical device. A suitable near field communications transceiver is disclosed in commonly assigned U.S. patent application Ser. No. 13/802,992, filed Mar. 14, 2013 by applicants Michael Hayes et al, and entitled COMMUNICATION SYSTEMS FOR PATIENT SUPPORT APPARATUSES, the disclosure of which is hereby incorporated herein by reference in its entirety.

Figure 10:
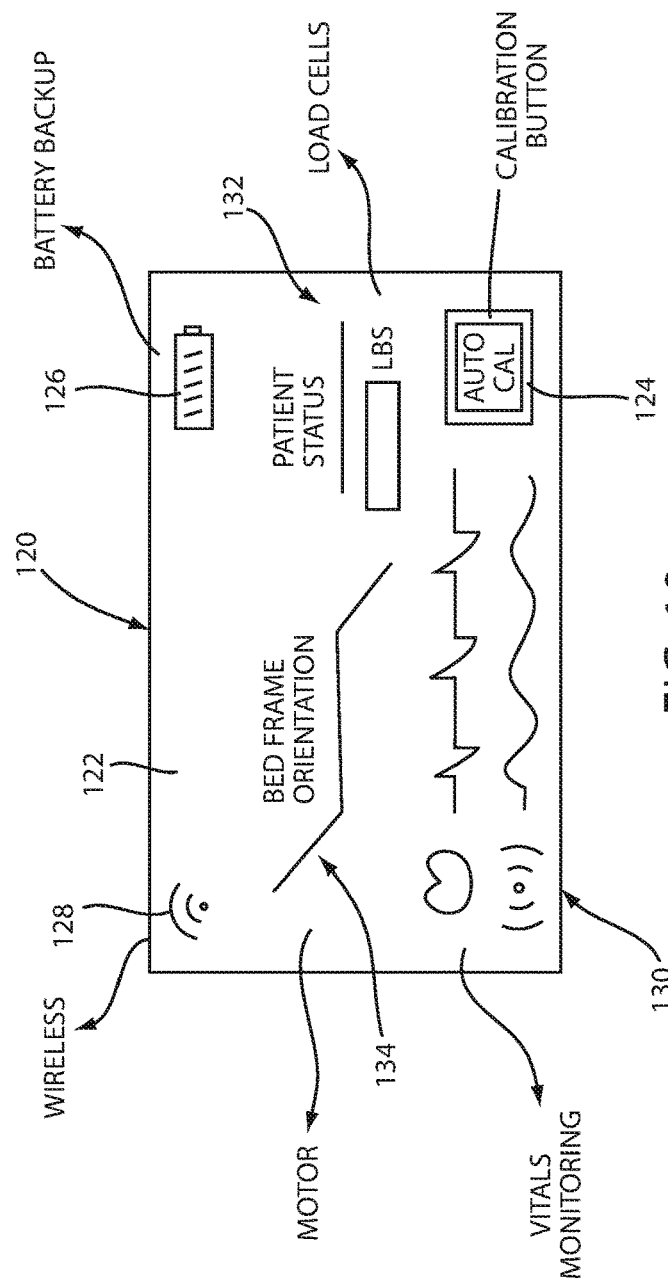
FIG. 10 is a schematic drawing of a user interface for a target detection system.

Referring to FIG. 10, the numeral 120 designates one embodiment of a user interface. For example, user interface 120 may comprise a display 122, including a touchscreen display. As noted above, control system 12 may indicate at the user interface when a component is coupled to the control system and therefore available for use by the user. Furthermore, as noted above, control system 12 may configure icons or buttons at the display, which may be used to control the component and/or simply indicate the status of the component.

As best seen in FIG. 10, display 122 comprises a button 124 that is configured as a start or start calibration button. For example, control system 12 may configure button 124 so that when it is depressed, control system 12 automatically detects the presence of components and makes the appropriate settings for the component, including configuring the display. Further, control system 12 may be configured to then automatically run any diagnostics and calibrate the component.

Control system 12 may also generate an icon 126 at display 122, which represents that a battery backup is available. For example, the icon may be in the form of a graphical representation of a battery and, further, may comprise markings, such as lines or color, which fill the body of the icon to indicate, for example, the remaining capacity of the battery. In addition, display 122 may comprise icons 128, 130, 132, 134 representing (1) a wireless connection is in use or available, (2) vital signs of a patient, such as heart rate, breathing rates, (3) patient status, such as weight, and (4) the motor or motors, for example, through a graphical representation of the bed frame configuration, respectively.

As described above, control system 12 may only enable icons for components that are connected to control system 12. The icons for components that are not detected may be disabled or may simply not be backlit, for example. For example, as described in U.S. Pat. App. Ser. No. 62/171,472, filed Jun. 5, 2015, entitled PATIENT SUPPORT APPARATUSES WITH DYNAMIC CONTROL PANELS (P477), the icon for an undetected component may not be visible. For example, the display may be physically constructed so that the icons selectively disappear for a given component when the component is not connected to control system 12, which is sometimes referred to as "dead fronting." As described in the referenced patent application, control system 12 deactivates the associated backlighting of one or more of icons or buttons, but with the icons reappearing when the component is detected by activating the corresponding backlights.

Accordingly, the detection system may consist of a variety of different systems including electrical detection systems, including a USB port, wireless detection systems, including an RFID tag reader, as well as optical detection systems, such as a barcode reader.

In yet another embodiment, the medical device comprises a temperature management system, including a pump. The component may be a thermal pad or a coolant or heater.

In yet another embodiment, the medical device comprises a hospital bed, and the component comprises a motor and brake status switch, with the detection system of the control system 12 detecting the status of the brake status switch.

In yet another embodiment, the medical device comprises a patient support, and the component comprises a holder for receiving a portable electronic device. The holder has a connection for connecting with the microprocessor 14 when a portable electric device is positioned in the holder and coupled to the connection so that the portable electronic device is then in communication with the microprocessor. Optionally, the microprocessor is configured to charge a portable electronic device when positioned in the holder. According to yet further aspects, the patient support comprises a display, which is in communication with the microprocessor and with the portable electronic device, when the portable electronic device is positioned in the holder and coupled to the connection. In this manner, a patient may operate the electronic portable electronic device through the display.

In another embodiment, the microprocessor is configured to activate or deactivate a function based on detecting the presence or absence of the component. For example, the microprocessor may be configured to activate or deactivate a diagnostic capability based on the absence of the component.

In any of the above, the microprocessor may be located at the medical device. Alternately, the microprocessor may be remotely located from the medical device.

While several forms of the disclosure have been shown and described, various alterations and changes can be made without departing from the spirit and broader aspects of the disclosure as defined in the appended claims, which are to be interpreted in accordance with the principles of patent law including the doctrine of equivalents. This disclosure is presented for illustrative purposes and should not be interpreted as an exhaustive description of all embodiments of the disclosure or to limit the scope of the claims to the specific elements illustrated or described in connection with these embodiments. For example, and without limitation, any individual element(s) of the described disclosure may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments comprise a plurality of features that are described in concert and that might cooperatively provide a collection of benefits. Also, as noted above the system of the present disclosure may be used on other pneumatic systems. Therefore, the present disclosure is not limited to only those embodiments that comprise all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

We claim:

1. A patient support comprising:
   a patient support based control system comprising:
      memory; and
      a microprocessor in communication with the memory;
   a detection system detecting installation of a component at the patient support and detecting communication of the component with the patient support based control system, the memory having stored therein a component setting associated with the component; and
   the patient support based control system establishing an association between the component and the patient support based control system when the detection system detects that the component is installed and is in communication with the patient support based control system, when the patient support based control system detects the component is installed and in communication with the patient support based control system the patient support based control system detecting a component identification of the component, selecting the component setting based on the component identification, and adjusting the component based on the component setting stored in the memory so that the component is suitable for use at the patient support.

2. The patient support according to claim 1, wherein the component comprises a temperature management apparatus, and the patient support based control system adjusting the temperature management apparatus based on the component setting stored in the memory when the temperature management apparatus is installed and in communication with the patient support based control system so that the temperature management apparatus is suitable for use at the patient support.

3. The patient support according to claim 2, wherein the temperature management apparatus comprises a heater or coolant.

4. The patient support according to claim 1, wherein the memory has a lookup table or a database, and the component setting stored in the lookup table or database.

5. The patient support according to claim 1, wherein the component comprises a pressure sensing mat or a deep vein thrombosis (DVT) component.

6. The patient support according to claim 1, further comprising a mattress, wherein the component comprises the mattress, the mattress comprises electronics, the patient support based control system adjusting the settings of the electronics based on the component setting stored in memory when the detection system detects the mattress is installed on the patient support so that the mattress is suitable for use at the patient support.

7. The patient support according to claim 1, wherein the component comprises electric brakes, the electric brakes having a motor and a brake status switch, the detection system operable to detect a position of the brake status switch.

8. The patient support according to claim 5, wherein the component comprises a motor, the detection system detecting the position of the motor.

9. The patient support according to claim 1, further comprising a holder for receiving a portable electronic device, the holder having a connection for connecting with the patient support based control system wherein when a portable electric device is positioned in the holder and coupled to the connection, the portable electronic device is in communication with the patient support based control system.

10. The patient support according to claim 9, wherein the patient support based control system is operable to charge a portable electronic device when positioned in the holder.

11. The patient support according to claim 9, wherein the patient support based control system further comprises a display, the display in communication with the microprocessor and with the portable electronic device when the portable electronic device is positioned in the holder and coupled to the connection, wherein a patient may operate the electronic portable electronic device through the display.

12. The patient support according to claim 1, wherein the patient support based control system activates or deactivates a function associated with the component based on detecting the presence or absence of the component.

13. The patient support according to claim 1, wherein the patient support based control system activates or deactivates a diagnostic capability based on the absence of the component.

14. The patient support according to claim 1, further comprising a user input interface in communication with the patient support based control system, and the user input interface operable to initiate the detection system detecting installation of the component.

15. The patient support according to claim 1, wherein the detection system auto-detects installation of the component.

16. A method of managing a component on a patient support, the method comprising the steps of:
providing a patient support with a patient support based control system, the patient based control system having memory and a component setting stored in the memory associated with the component;
detecting installation of the component at the patient support and communication of the component with the patient support based control system;
detecting a component identification of the component;
selecting the component setting based on the component identification; and
the patient support based control system adjusting the component settings of the component using the component setting stored in the memory based on the component identification when the component is detected as being installed at the patient support and in communication with the patient support based control system control system.

17. The method of managing a patient support according to claim 16, wherein the detecting installation comprises detecting a signal from the component.

18. The method of managing a patient support according to claim 16, further comprising displaying an icon at the patient support representative of the component.

19. The method of managing a patient support according to claim 18, wherein the displaying comprises displaying a characteristic of the component at the patient support.

20. The method of managing a patient support according to claim 17, further comprising transmitting with the signal the component identification.

21. The patient support according to claim 1, wherein the memory includes a plurality of component settings, and the patient support based control system selecting the component setting from the plurality of component settings based on the component identification.

* * * * *